US012502566B2

(12) United States Patent
Ohtake

(10) Patent No.: US 12,502,566 B2
(45) Date of Patent: Dec. 23, 2025

(54) MASK PACKAGE

(71) Applicant: DAIO PAPER CORPORATION, Ehime (JP)

(72) Inventor: Yuya Ohtake, Tochigi (JP)

(73) Assignee: DAIO PAPER CORPORATION, Ehime (JP)

( * ) Notice: Subject to any disclaimer, the term of this patent is extended or adjusted under 35 U.S.C. 154(b) by 0 days.

(21) Appl. No.: 18/844,114

(22) PCT Filed: Mar. 22, 2023

(86) PCT No.: PCT/JP2023/011161
§ 371 (c)(1),
(2) Date: Sep. 5, 2024

(87) PCT Pub. No.: WO2023/199708
PCT Pub. Date: Oct. 19, 2023

(65) Prior Publication Data

US 2025/0177787 A1 Jun. 5, 2025

(30) Foreign Application Priority Data

Apr. 14, 2022 (JP) ................................ 2022-066773

(51) Int. Cl.

| | |
|---|---|
| ***B65D 81/24*** | (2006.01) |
| ***A61L 9/012*** | (2006.01) |
| ***A62B 25/00*** | (2006.01) |
| ***B65D 75/30*** | (2006.01) |

(52) U.S. Cl.
CPC .............. *A62B 25/00* (2013.01); *A61L 9/012* (2013.01); *B65D 75/30* (2013.01)

(58) Field of Classification Search
CPC .... B65D 75/30; B65D 75/54; B65D 75/5855; B65D 33/1608; B65D 77/04; B65D 83/08; A45D 44/002; A41D 13/11
USPC .............................. 206/205, 213, 213.1, 494
See application file for complete search history.

(56) References Cited

U.S. PATENT DOCUMENTS 5,458,244 A * 10/1995 Emori .................... B65D 83/00 206/219
6,357,260 B1 * 3/2002 Lutz ..................... A44C 15/002 63/DIG. 2
2004/0222108 A1 * 11/2004 Tommarello ........... A61B 50/30 206/438
2004/0238656 A1 * 12/2004 Wang ........................ A61L 9/12 239/34

(Continued)

FOREIGN PATENT DOCUMENTS

JP H07-059836 3/1995
JP 2001-231846 8/2001
JP 2004-180959 7/2004

(Continued)

OTHER PUBLICATIONS

Patent Translate, Bibliographic data: JP2004180959; Jul. 2, 2004; Aroma Device; 8 pages.*

(Continued)

*Primary Examiner* — Luan K Bui
(74) *Attorney, Agent, or Firm* — IPUSA, PLLC

(57) ABSTRACT

A mask package includes: a mask; a package configured to enclose the mask; and a bag placed in the package and enveloping a fragrance carrier carrying a fragrance.

6 Claims, 6 Drawing Sheets

(56) References Cited

U.S. PATENT DOCUMENTS

| | | | | |
|---|---|---|---|---|
| 2008/0230066 | A1 * | 9/2008 | Chandaria .............. | A41D 13/11<br>128/206.13 |

FOREIGN PATENT DOCUMENTS

| | | |
|---|---|---|
| JP | 2005-021548 | 1/2005 |
| JP | 2014-054509 | 3/2014 |
| JP | 2017-217063 | 12/2017 |
| JP | 2022-013617 | 1/2022 |

OTHER PUBLICATIONS

International Search Report for PCT/JP2023/011161 filed on Jun. 13, 2023.

* cited by examiner

MASK PACKAGE

TECHNICAL FIELD

The present invention relates to a mask package.

BACKGROUND ART

It is known to apply a fragrance ingredient to a mask. For example, PTL 1 sets forth a mask in which the mask body includes a fragrance-containing nonwoven fabric sheet, and the fragrance-containing nonwoven fabric sheet contains microcapsules containing a fragrance such as menthol.

CITATION LIST

Patent Literature

[PTL 1] Japanese Patent Application Laid-Open Publication No. 2014-54509

SUMMARY OF THE INVENTION

Technical Problem

However, in the above-described form of the fragrance encapsulated in microcapsules, a sufficient scent is not generated unless an impact such as tapping the mask body is applied, and the wearer may not be able to perceive the scent in the initial stage of wearing. In addition, although it is conceivable to directly apply the fragrance to the mask body, the initial amount of the fragrance to be applied cannot help being high, taking into consideration volatilization of the fragrance ingredient during storage of the mask before use. In such a case, the fragrance may smell too strong in the initial stage of wearing and spoil the comfort.

In view of the above, it is an object of an embodiment of the present invention to provide a mask from which a scent of a moderate strength can be smelled even at an initial stage of wearing.

Solution to the Problem

An embodiment of the present invention is a mask package, including: a mask; a package configured to enclose the mask; and a bag placed in the package and enveloping a fragrance carrier carrying a fragrance.

Advantageous Effects of the Invention

According to one embodiment of the present invention, it is possible to provide a mask from which a scent of a moderate strength can be smelled even at an initial stage of wearing.

DETAILED DESCRIPTION OF THE INVENTION

Figure 1:
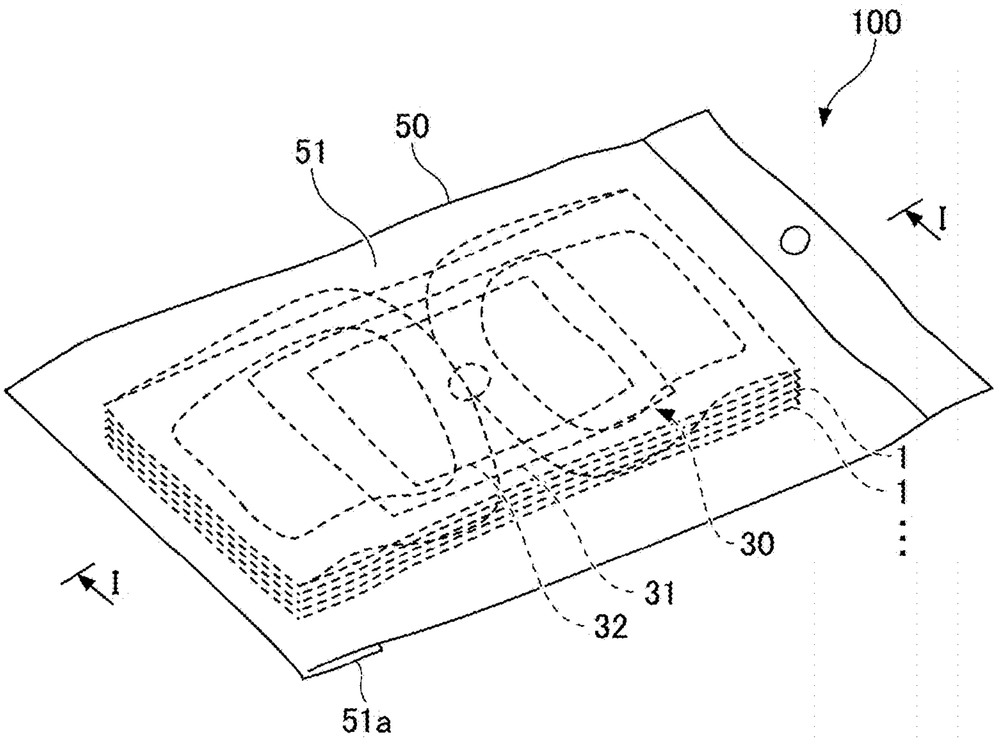
FIG. 1 is a perspective view of a mask package according to the present embodiment.

Embodiments of the present invention will now be described in detail with reference to the drawings. Unless otherwise noted, the same or corresponding components in the drawings will be denoted by the same reference numerals, and the description thereof may be omitted.

<Mask Package>

Figure 2:
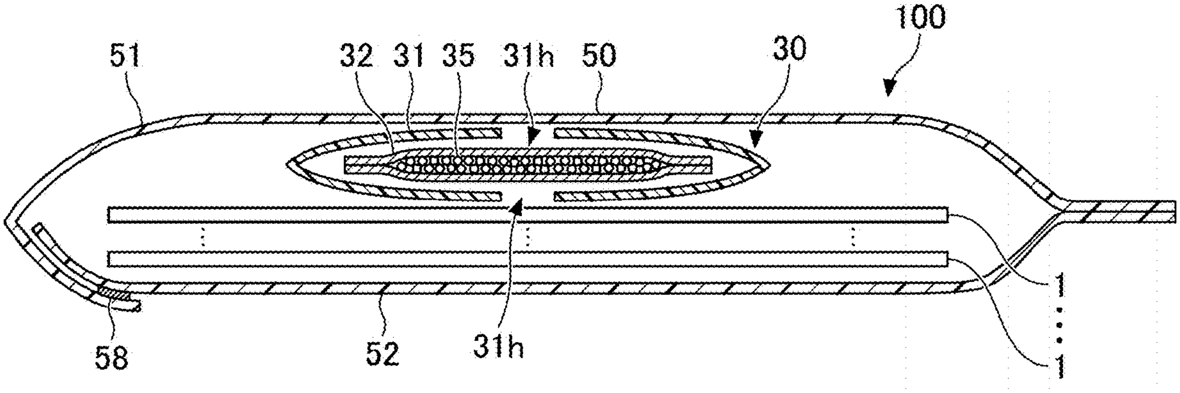
FIG. 2 illustrates an exemplary cross-sectional view taken along a line I-I of FIG. 1.

FIG. 1 is a perspective view of a mask package (i.e., a package in which a mask is enclosed) 100 according to the present embodiment. FIG. 2 is a cross-sectional view of FIG. 1 taken along a line I-I. As illustrated in FIG. 1, the mask package 100 according to the present embodiment includes a mask 1 capable of covering the face of a wearer, more specifically, at least the nose and the mouth of the wearer, and a package 50 in which the mask 1 is enclosed. The package 50 according to the present embodiment may be used to enclose a mask before the start of use, or may be used to temporarily enclose a mask that has already started to be used. Further, one mask may be enclosed in one package 50, or a plurality of masks 1, 1, . . . may be enclosed as illustrated in FIG. 1. When a plurality of masks 1, 1, . . . are enclosed, the number of masks may be from 2 through 10.

The mask 1 according to the present embodiment is also referred to as a sanitary mask or a surgical mask that may have a function of preventing foreign matter from coming on the face or preventing splashing of droplets exhaled by the wearer. The mask 1 may be disposable or can be repeatedly used by washing. The mask 1 includes a mask body (hereinafter may also be referred to simply as "body") that is placed in front of the face of the wearer during wearing and can mainly cover the nose and the mouth of the wearer, and a pair of ear hooks joined to the left and right ends of the mask body, respectively.

<Package>

The form of the package 50 is not particularly limited as long as it has a structure that covers the entirety of the mask 1 and does not allow fingers or foreign matter to enter the package 50 easily by mistake, but it is preferable that the package has sealability. In the present specification, sealability does not necessarily mean airtightness, but may be a property that inhibits or delays volatilization of volatile ingredients placed inside the package. As illustrated in FIG. 1, the package 50 may be configured as an envelope-shaped package formed of a film or sheet. In a case where the package 50 is an envelope-shaped package, a first sheet 51 and a second sheet 52 are overlaid on each other as the package 50 and are joined with each other on the periphery except for a part, and the mask 1 is placed in the center. The first sheet 51 may be configured to protrude more than the second sheet 52 at the mentioned part, i.e., the part of the periphery where the sheets are not joined, and a protrusion 51*a* is folded back and placed on the second sheet 52. The protrusion (or folded part) 51*a* may be adhesively attached to the outer surface of the second sheet 52 detachably via a tacky agent 58. Such an envelope-shaped package is preferable because it is relatively easy to manufacture and is not bulky.

Although the material of the sheets 51 and 52 constituting part of the package 50 are not particularly limited, it is preferable that they are airtight (gas-impermeable) materials from the viewpoint of making it difficult to dissipate a fragrance ingredient (described in detail later) to the outside. Accordingly, the sheets 51 and 52 constituting part of the package 50 preferably contain a polymer film. Examples of the polymer film include: films formed of polyester (PES) such as oriented polypropylene (OPP), cast polypropylene (CPP), polyethylene (PE), polyvinyl chloride (PVC), polyester, polyamide (PA), polyethylene terephthalate (PET), polybutylene terephthalate (PBT), and the like, an ethylene-vinyl alcohol copolymer (EVOH), and the like; an aluminum deposited film obtained by vapor-depositing a metal, e.g., aluminum on the mentioned polymer films; and the like. The films can be used alone, or can be used as a laminated film in which a plurality of films are combined, for example, a plurality of films are stacked and pasted to each other. In the case of the present embodiment, it is preferable to use a laminated film containing an oriented polypropylene (OPP) film and an aluminum-deposited cast polypropylene (CPP) film because of its excellent moisture resistance, light shielding properties, and strength.

<Fragrance Carrier>

As illustrated in FIGS. 1 and 2, a fragrance carrier 35 carrying a fragrance is placed inside the package 50 while being filled in a bag 30. In other words, the fragrance carrier 35 is developed in the bag 30. In the example illustrated in FIGS. 1 and 2, in the package 50, the bag 30 filled with the fragrance carrier 35 (also referred to as the fragrance carrier-filled bag) is positioned between a bundle of masks 1, 1, . . . and the package 50. In this case, it is preferable that the bag 30 is positioned so as to face the face side of the mask 1 (the side made to face the face of the wearer during wearing). When a plurality of masks 1, 1, . . . are enclosed in the package 50, the bag 30 may be positioned between the masks 1, 1.

In the example illustrated in FIGS. 1 and 2, the number of the bags 30 filled with the fragrance carrier 35 (fragrance carrier-filled bag) is 1 for a package 50, but may be 2 or more. When the number of the bags 30 filled with the fragrance carrier 35 is 2, the two bags 30 may be positioned on both sides of the bundles of the masks 1, 1, and . . . , i.e., the two bags 30 may be positioned to sandwich the bundles of the masks 1, 1, and . . . therebetween.

The carrier constituting part of the fragrance carrier 35 is preferably, for example, an inorganic porous body, because the porous body and the fragrance have a low reactivity. Examples of the porous body include inorganic oxides, for example, silicon oxide such as silica gel, calcium silicate, zeolite, bentonite, and the like. Of these, silica gel is preferable because it is relatively inexpensive and has excellent moisture absorption. The BET specific surface area of the carrier may be from 30 $m^2/g$ through 2,000 $m^2/g$ and the average pore diameter of the carrier may be from 0.2 nm through 30 nm. The porous body is preferably a particle aggregate having an average particle diameter of from 1 mm through 10 mm. The particle aggregate can fluidize in the bag 30. Therefore, when the package 50 is moved, the bag 30 also moves and the particles in the bag fluidize, such that volatilization and dissipation of the fragrance ingredient can be promoted.

In the fragrance carrier 35, the fragrance carried on the carrier is not particularly limited, and may be a natural fragrance or a synthetic fragrance. Specific examples of fragrances include natural fragrances such as peppermint oil, spearmint oil, eucalyptus oil, lemon oil, grapefruit oil, rosemary oil, mandarin oil, lime oil, citron oil, chamomile oil, lavender oil, rose oil, myrtle oil, tea tree oil, and the like, terpenes such as menthol, camphor, limonene, pinene, linalool, citronellol, geraniol, and the like, and synthetic fragrances such as alcohols, ketones, and aldehydes. These fragrances may be used alone or in combination of two or more. Among the fragrances listed above, mint-based oils, menthol, camphor, and the like, which can physiologically make a person smelling them feel a sense of coolness or a sense of coldness, are preferable.

The fragrance carrier can be obtained, for example, by placing porous particles in a rotary mixer, adding a fragrance in a state of being diluted with a solvent, or the like, and stirring them. In this case, the amount of the fragrance used may be from 3 parts by mass through 20 parts by mass relative to 100 parts by mass of the porous particles.

<Bag>

The bag 30 is configured to enable the accommodated fragrance ingredient to be volatilized and released to the outside of the bag 30. Thus, since the fragrance carrier 35 is accommodated in the bag 30, direct contact between the fragrance and the mask 1 can be avoided, and the fragrance ingredient, once released into the package 50, can mix with the air in the package 50, can be carried by the air at a moderate concentration, and can attach to the mask 1. Therefore, compared with the case where the fragrance is directly applied to the mask, the fragrance ingredient can be provided to the mask at a moderate concentration over a wide range. Therefore, the material of the bag 30 may be, for example, a fiber structure in which fibers are aggregated or a gas-permeable film, which can be easily permeated by a gas.

In the present embodiment, the fragrance is also separated from the package 50 by the bag 30 and is not in direct contact with the package 50. Therefore, the fragrance or the solvent used for applying the fragrance can reduce its effects on the material of the package 50. For example, when a laminate film as described above is used as the material of the package 50, an adhesive agent at the junction between the films, used for forming the laminate film, may be affected by the fragrance or the solvent, and the laminate film may peel. Here, there is no such concern in the present embodiment in which the fragrance is not directly applied to the package 50.

In addition, the bag 30 filled with the fragrance carrier 35 can be manufactured as a separate body from the package 50 described above. Therefore, in manufacture of the mask package 100, the package 50 can be manufactured first, and then the mask 1 and the bag 30 filled with the fragrance carrier 35 may be enclosed in the package 50 afterwards. That is, presence of a fragrance is not necessary in the manufacturing process of the package 50. This provides the following advantages. In a case where a fragrance is present in the manufacturing process of the package, such as when a fragrance is one of the materials of the package, there is a concern that the fragrance will remain in the equipment after manufacturing. Therefore, it may be necessary to construct a dedicated manufacturing line for the package. As compared with this, according to the present embodiment, no concerns about the fragrance are needed when manufacturing the package. This is advantageous in terms of labor and cost.

As illustrated in FIGS. 1 and 2, the bag 30 includes an outer bag 31 and an inner bag 32, and the above-mentioned fragrance carrier 35 may be accommodated in the inner bag 32. By forming the bag 30 as such a double structure, different functions can be provided to the outer bag 31 and the inner bag 32, and the functions of the whole bag 30 can be improved.

Figure 3:
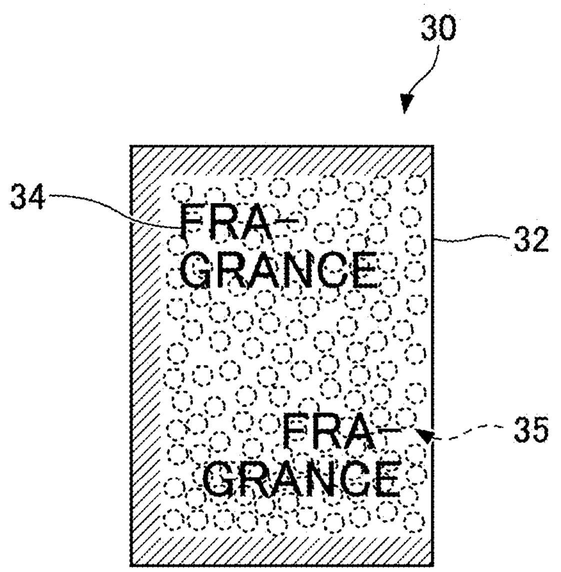
FIG. 3 illustrates a plan view of an inner bag.
Figure 4:
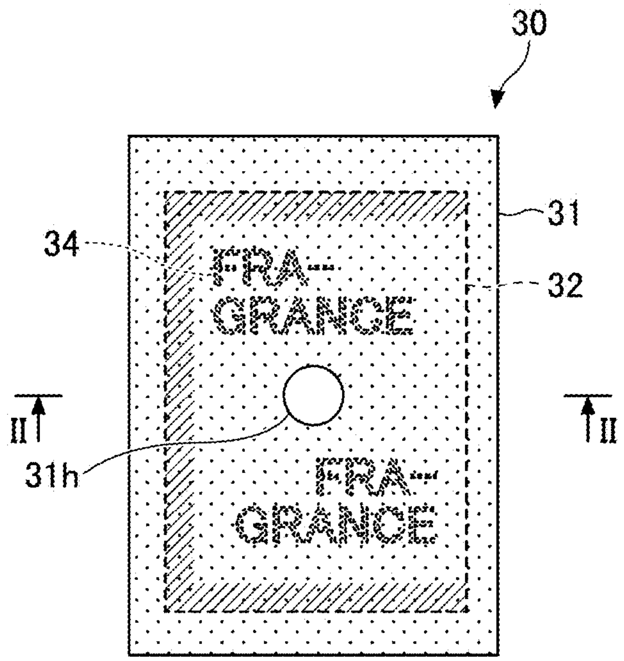
FIG. 4 illustrates a plan view of a bag.
Figure 5:
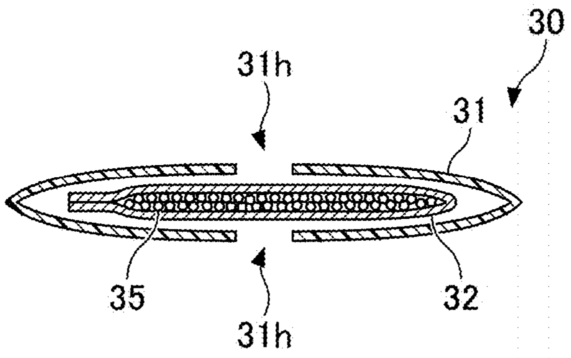
FIG. 5 illustrates an exemplary cross-sectional view taken along a line II-II of FIG. 4.

FIG. 3 illustrates a plan view of only the inner bag 32. FIG. 4 illustrates a plan view of the bag 30 formed of the outer bag 31 and the inner bag 32, and FIG. 5 illustrates a cross-sectional view of FIG. 4 taken along a line II-II. The outer bag 31 is expressed in gray or pearskin finish in FIG. 4, yet the outer bag 31 is preferably transparent or semi-transparent (as described later). In FIG. 4, the filled fragrance carrier 35 is not illustrated.

<Inner Bag>

The inner bag 32 may be made of a fiber structure. The fiber structure is preferable because of its high strength against tearing and tension and its high air permeability. The fiber structure, of which the inner bag 32 is made, is not particularly limited, so long as it is a structure in which fibers are assembled into a sheet, and may be a nonwoven fabric, fabric, knitted fabric, or the like. The fibers, of which the fiber structure is made, may be natural fibers, synthetic fibers, or a mixture thereof. Of these, nonwoven fabrics are preferable because the fibers can be closely structured three-dimensionally, and nonwoven fabrics are available at a low price. When the inner bag 32 is a nonwoven fabric, it may be a spunbond nonwoven fabric, a spunlace nonwoven fabric, a melt-blown nonwoven fabric, an airthrough nonwoven fabric, a point bond nonwoven fabric, or the like. When the nonwoven fabric is made of resin fibers, the type of the resin may be polyethylene, polypropylene, polyethylene terephthalate, nylon, or the like.

When the bag 30 is formed of the outer bag 31 and the inner bag 32, the inner bag 32 is loaded with the fragrance carrier 35.

As illustrated in FIGS. 3 and 4, the outer surface of the inner bag 32 may be provided with information 34 about either or both of: the fragrance or the fragrance carrier 35; and the bag 30. In the examples illustrated in FIGS. 3 and 4, the above information 34 is provided by the letters "FRAGRANCE". However, as long as the function of the bag 30, that is, the function as a fragrance bag (fragrance sachet), can be recognized when viewed by the user, the information may include not only letters but also illustrations, symbols, and the like. In addition, the information 34 may include the type of the fragrance, the manufacturer, handling precautions (for example, warning against being eaten), and the like.

It is possible to add the information 34 by printing of an ink containing a colorant, pasting, sewing, or the like of a sheet containing the information 34. Among these, printing of an ink is preferable because it is a simple method. When adding the information 34 by printing, the ink to be used may be a publicly known ink suited to the material for forming the inner bag 32.

The timing at which information 34 is added to the outer surface of the inner bag 32 may be before or after the fragrance carrier 35 is accommodated in the inner bag 32. For example, by preparing a fiber structure (fiber structure sheet), to one surface of which the information 34 is previously added, enveloping the fragrance carrier 35 in the fiber structure such that the surface to which the information 34 is added becomes the outer surface, and sealing the periphery of the fiber structure by such means as a heat seal, an adhesive agent, or the like, it is possible to envelop the fragrance carrier 35. As a result, the inner bag 32 containing the fragrance carrier 35 is produced. As a means for sealing the periphery of the fiber structure, a heat seal is preferable from the viewpoint of reducing the probability that interaction will occur between the fragrance and the adhesive agent, and an adhesive agent is preferable from the viewpoint of reducing the effects of heat to be received by the fragrance.

As illustrated in FIGS. 3 and 4, the plan-view shape of the inner bag 32 is preferably quadrangular, especially rectangular. Similarly, the plan-view shape of the entirety of the mask 1 and the plan-view shape of the package 50 are preferably rectangular. It is possible to form the quadrangular inner bag 32 illustrated in FIGS. 3 and 4 from one fiber structure sheet without wasting any part of the sheet. When the plan view shape of the inner bag 32 is quadrangular, the length of one side is not particularly limited so long as it is a size that does not fall out of the package 50 and the outer bag 31 described later, yet is preferably from 30 mm through 100 mm.

<Outer Bag>

The outer bag 31 can be provided on the outer side of the inner bag 32. With the outer bag 31 positioned on the outer side of the inner bag 32, the bag 30 is doubled. As a result, since the inner bag 32 is protected by the outer bag 31, the risk of the contained fragrance carrier 35 popping out can be reduced in the event that the inner bag 32 is torn during conveying or grasping the bag 30 during the manufacturing process of the mask package 100.

The plan-view shape and size of the outer bag 31 are not particularly limited so long as the inner bag 32 can be accommodated. The plan-view shape of the outer bag 31 is preferably the same as that of the inner bag 32. In the example illustrated in FIG. 4, the plan-view shape of the outer bag 31 is preferably quadrangular, and more preferably rectangular like the inner bag 32. When the plan-view shape of the outer bag 31 is quadrangular, the length of one side thereof is not particularly limited as long as it is a size that can accommodate the inner bag 32 and does not fall out of the package 50, yet is preferably from 50 mm through 130 mm.

The outer bag 31 is preferably made of a polymer film. When the information 34 is added to the outer surface of the inner bag 32 as described above, the outer bag 31 is preferably transparent or semi-transparent such that the information 34 can be visually recognized. The material for forming the outer bag 31 may be gas-permeable or gas-impermeable, but it is preferable to use a gas-impermeable film from the viewpoint of controlling costs and ensuring transparency (visibility of the inner bag 32).

Specific examples of the polymer film forming the outer bag 31 include: polyester (PES) such as oriented polypropylene (OPP), cast polypropylene (CPP), polyethylene (PE), polyvinyl chloride (PVC), polyester, polyamide (PA), polyethylene terephthalate (PET), polybutylene terephthalate (PBT), and the like; an ethylene-vinyl alcohol copolymer (EVOH); and the like. Of these, oriented polypropylene (OPP) is preferable, and more specifically, biaxially oriented polypropylene is preferable, because sufficient transparency is obtained, and moisture resistance and strength are excellent.

The outer bag 31 can also be used to control the release rate of the fragrance ingredient to be released from the fragrance carrier accommodated in the inner bag 32. For example, by using a gas-impermeable or low-gas-permeable film as the outer bag 31 and making a hole 31*h* (FIGS. 4 and 5) in the outer bag 31, it is possible to adjust the release of the fragrance ingredient in accordance with the shape, size, number, and position of the hole.

In the example illustrated in FIGS. 4 and 5, one circular hole 31*h* is formed in the outer bag 31 approximately in the center of the outer bag 31 in a plan view, but the shape and size of the hole are not limited to those illustrated. When the information 34 is added to the surface of the inner bag 32 with a coloring agent as described above, it is preferable that the hole in the outer bag 31 is formed such that the portion to which the information 34 is added remains covered by the outer bag 31, that is, the portion to which the coloring agent is distributed is not exposed through the hole 31*h*. Alternatively, it is preferable that the information be added such that the coloring agent to be applied to the outer surface of the inner bag 32 for adding the information 34 is not exposed through the hole in the outer bag 31. In the example illustrated in FIG. 4, the information 34 added to the outer surface of the inner bag 32, i.e., the portion marked with the letters "fragrance", is not exposed through the hole 31*h* formed in the outer bag 31.

The hole formed in the outer bag 31 may be formed only in one surface of the outer bag 31, or may be formed as illustrated in FIGS. 2, 4, and 5. Since the holes 31*h* and 31*h* are formed in each surface of the outer bag 31 as illustrated in FIGS. 2, 4, and 5, the distance from the hole 31*h* to the mask 1 is approximately the same regardless of which surface of the bag 30 is faced with the mask 1 in the package 50. Hence, the step of detecting which surfaces of the bag 30 are the outer surface or the inner surface, and adjusting them in the right place is unnecessary when enclosing the bag 30 in the package 50.

In a case where holes are formed in the outer bag 31, the total area of the holes is preferably from 5% through 20% of the plan-view area of the inner bag 32. By adjusting the area of the holes within the above range, it is possible to sufficiently release the fragrance ingredient outside the outer bag 31, to maintain the strength of the entire outer bag 31, and to reduce the probability that the ink exposed through the holes 31*h* will adhere to the inner wall of the package or to the mask 1 in a case where the information 34 is added to the outer surface of the inner bag 32 with the ink as described above.

The size of one hole 31*h* formed in the outer bag 31 may be from 1 mm through 20 mm as an equivalent circle diameter, although depending on the number, arrangement, and the like of the holes. The equivalent circle diameter means the diameter of a true circle having the same area as the area of the hole 31*h* regardless of the shape of the hole 31*h*. As illustrated in FIGS. 4 and 5, when the number of holes 31*h* formed in one surface is 1, the equivalent circle diameter of the hole 31*h* is preferably from 5 mm through 15 mm. Further, although the shape of the hole 31*h* illustrated in FIG. 4 is circular, the shape of the hole 31*h* may not necessarily be circular, and may be polygonal, such as an ellipse, a quadrangle, a triangle, and the like, or any other desirably selected shape (for example, a heart shape, a drop shape, and the like).

<Modified Example of Outer Bag>

Figure 6:
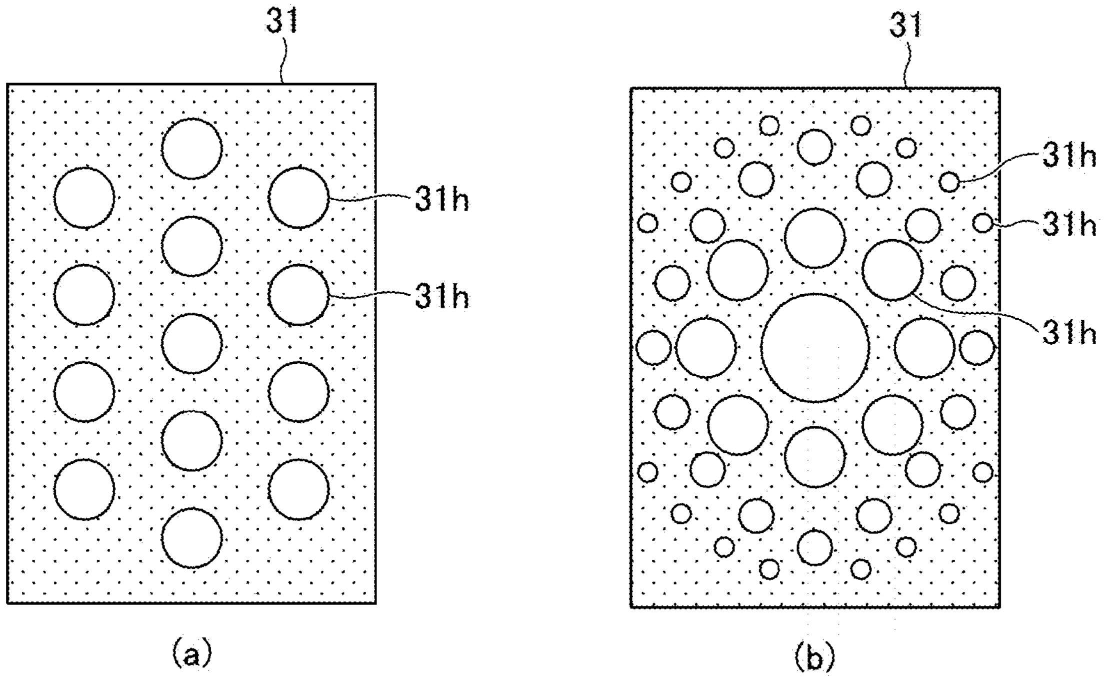
FIG. 6 illustrates a modified example of a bag.

FIG. 6 illustrates a modified example of the hole formed in the outer bag 31. FIG. 6 illustrates a plan view of only the outer bag 31. FIG. 6 also illustrates the outer bag 31 in gray (pearskin finish), but the outer bag 31 is preferably transparent or semi-transparent as described above. As illustrated in FIG. 6, a plurality of holes 31*h*, 31*h*, . . . may be formed in one surface of the outer bag 31. In this case, the plurality of holes 31*h*, 31*h*, . . . may have the same size as each other as illustrated in FIG. 6 (*a*) or may be varied in size from each other as illustrated in FIG. 6 (*b*).

In both the example illustrated in FIG. 6 (*a*) and the example illustrated in FIG. 6 (*b*), the plurality of holes 31*h*, 31*h*, . . . are formed not only in the center but also over the entire surface of the outer bag 31. As a result, the fragrance ingredient can be released not only from the center but also from the entire surface of the bag 30, and the interior of the package 50 can be quickly filled with a fragrance ingredient in the in-plane direction even if it is a slow-release fragrance.

In the example illustrated in FIG. 6 (*a*), the holes 31*h*, 31*h*, . . . of the same shape and size are formed in a staggered shape, such that the fragrance ingredient is easily released uniformly from the entire surface of the outer bag 31. Further, in the example illustrated in FIG. 6 (*a*), even if a wrong position is punched by a punching molder for forming the holes 31*h*, 31*h*, . . . in the manufacturing process of the outer bag 31, the holes 31*h*, 31*h*, tend to be kept effective.

In the example illustrated in FIG. 6 (*b*), the shape of the holes 31*h*, 31*h*, . . . is circular, which is the same as above, but the size of the holes 31*h* is varied depending on the position. The size of the holes 31*h* is smaller at positions closer to the periphery of the outer bag 31, and is larger at positions farther from the periphery (i.e., at positions closer to the center). When the fragrance carrier 35 is a particle aggregate, the fragrance carrier 35 moves in the inner bag 32 and tends to be densely distributed in the center. Therefore, forming the holes 31*h*, 31*h*, illustrated in FIG. 6 (*b*) in the outer bag 31 is preferable in a case where it is desired that the fragrance ingredient will be released as quickly as possible while it is also desired that the fragrance ingredient will be released from the entire surface of the outer bag 31.

In the example of the outer bag 31 described above, the outer bag 31 has a hole, that is, a removed part that is formed from a part of the outer bag 31 being removed, but the outer bag 31 may have a cut instead of a hole. Here, the cut refers to a product that is formed by a process of simply making a cut without removing the material from the outer bag 31 (i.e., without generating a removed debris). The fragrance ingredient released outside the inner bag 32 is further released outside the outer bag 31 through the cut and can fill the air in the package 50.

The outer bag 31 and the inner bag 32 may or do not need to be fixed to each other. The bag 30 may also be a laminate formed by pasting the material of the outer bag 31 and the material of the inner bag 32 with each other.

<Mask>

Figure 7:
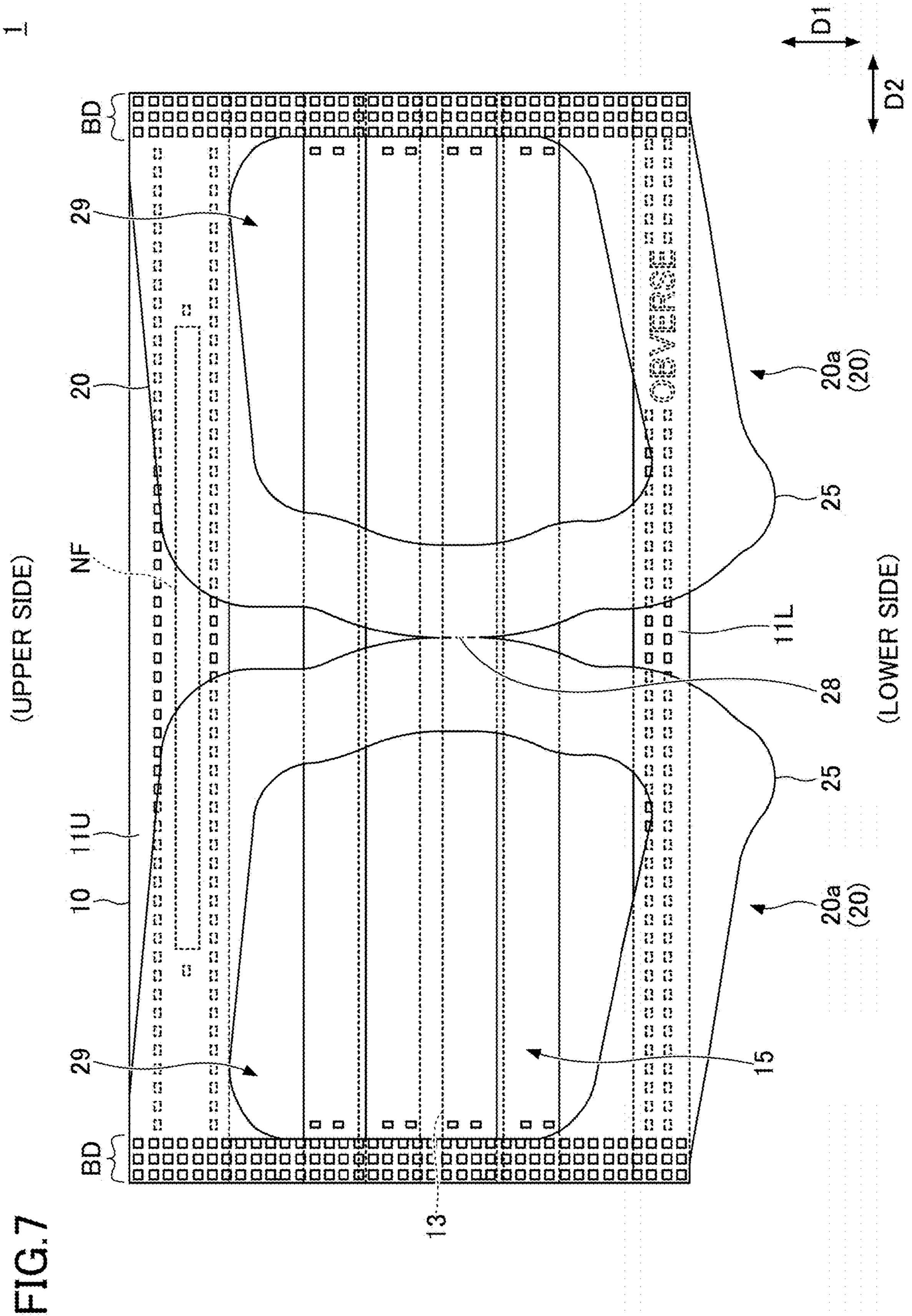
FIG. 7 is a plan view of a mask before use according to the present embodiment.
Figure 8:
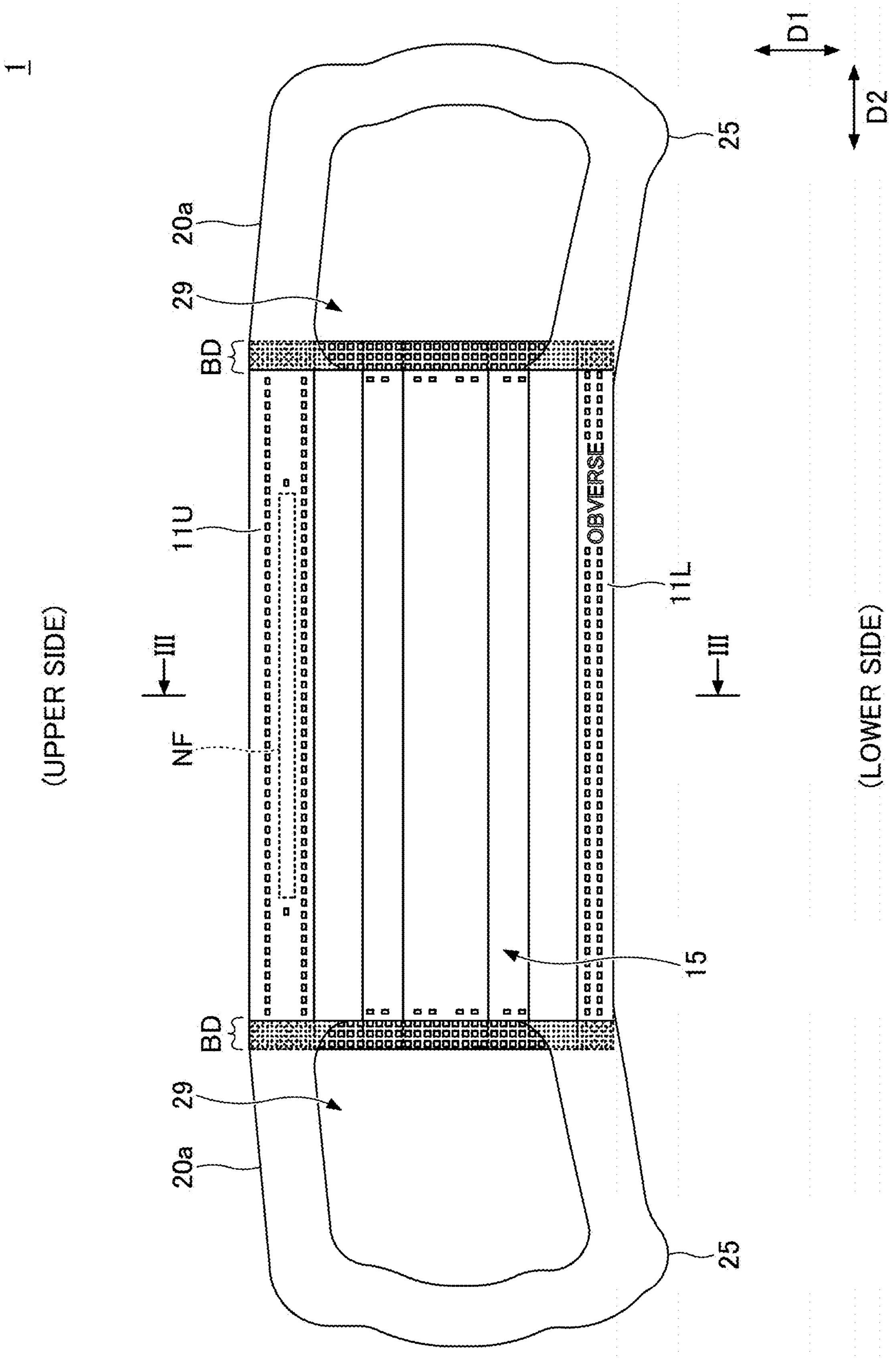
FIG. 8 is a plan view of the mask illustrated in FIG. 6 with ear hooks opened.

In the present embodiment, the configuration of the mask enclosed in the package 50 is not particularly limited, but an example of the mask 1 will be illustrated with reference to FIGS. 7 to 9. FIG. 7 is a plan view of the mask 1 viewed from the outer side (a side opposite to a side to be faced with the face of the wearer during wearing, i.e., a side opposite to the face side). As illustrated in FIG. 7, the mask 1 includes a mask body 10 and a pair of ear hooks 20*a* and 20*a*. The mask 1 and the mask body 10 have an upper-lower (vertical direction) D1 corresponding to the upper-lower direction of the face of the wearer during wearing, and a left-right direction (horizontal direction) D2 corresponding to the left-right direction of the face of the wearer during wearing. The vertical direction D1 and the horizontal direction D2 are orthogonal to each other. FIG. 8 is a plan view illustrating a state in which the ear hooks 20*a* and 20*a* are opened in the left-right direction in order to use the mask 1, and FIG. 9 is a cross-sectional view of the mask body 10 (a cross-sectional view of FIG. 8 along a line III-III).

Figure 9:
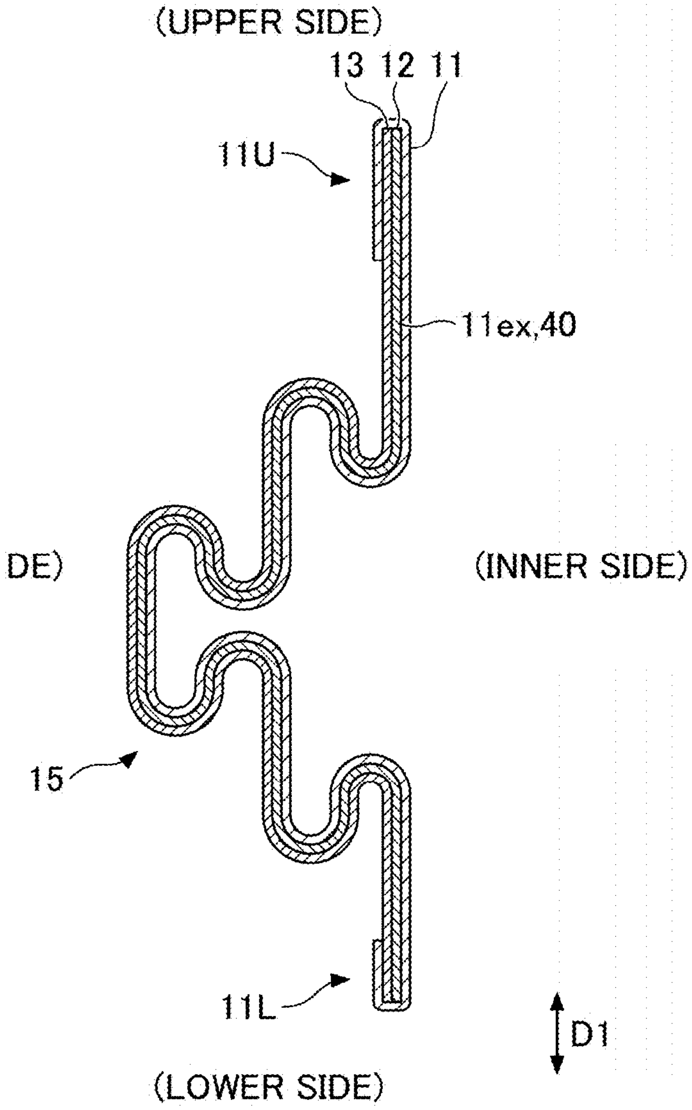
FIG. 9 is an exemplary cross-sectional view of a mask body (taken along a line III-III of FIG. 8).

In the example illustrated in FIGS. 7 to 9, the mask body 10 has a rectangular plan-view shape having a longer side in the horizontal direction D2, but the plan-view shape of the mask body 10 is not limited to that illustrated. As illustrated in FIGS. 7 to 9, the mask body 10 has a pleated structure 15 formed by a plurality of folds (pleats) arranged side by side in the vertical direction D1. The folds of the pleated structure 15 are formed by folding a sheet constituting the mask body 10 along folding lines that are along the horizontal direction D2. In the state in which the plurality of folds are formed, both ends of the mask body 10 in the horizontal direction D2 are fixed by a heat seal, an ultrasonic seal, an adhesive agent, or the like. In this example, the pleated structure 15 is formed such that the center in the vertical direction D1 becomes box-pleated (FIG. 9), but the specific configuration of the pleated structure 15 is not particularly limited and may be a publicly-known configuration that is formed on a mask body.

The mask body 10 may have a multilayer structure in which a plurality of sheets are laminated. The mask body 10 may have a three-layer structure in which an inner sheet (face-facing sheet) 11, an intermediate sheet 12, and an outer sheet 13 are laminated in the order from the inner side. Preferably, each of the sheets constituting the mask body 10 includes a fiber structure such as a nonwoven fabric, a woven fabric, a knitted fabric, and the like. Of these, the nonwoven fabric has a structure in which fibers are intricately intertwined, and is preferable from the viewpoint that it is highly functional in collecting foreign matter (dust, pollen, bacteria, viruses, and the like), and that retention of the fragrance ingredient released from the fragrance carrier 35 and coming to the mask body 10 is facilitated.

Examples of the nonwoven fabric from which the mask body 10 is made include spunbond nonwoven fabric, spunlace nonwoven fabric, melt blown nonwoven fabric, air-through nonwoven fabric, point bond nonwoven fabric, and the like. Since it is preferable to enhance the intermediate sheet 12 in the function of collecting foreign matter, it is preferable to use a melt blown nonwoven fabric that may contain thin fibers. It is preferable that the fibers constituting the nonwoven fabric are resin fibers, and examples of the resin types of the resin fibers include polyethylene, polypropylene, polyethylene terephthalate, nylon, and the like. The inner sheet (face-facing sheet) 11 and the outer sheet 13 may have a weight of from 10 $g/m^2$ through 50 $g/m^2$. The weight of the intermediate sheet having a high foreign matter collectability is preferably from 10 $g/m^2$ through 100 $g/m^2$, may be from 10 $g/m^2$ through 50 $g/m^2$, and is more preferably from 15 $g/m^2$ through 50 $g/m^2$.

In the present embodiment, the mask body 10 is folded back on the upper and lower sides. More specifically, the inner sheet (face-facing sheet) 11 has a length that makes the upper end and lower end protrude from the intermediate sheet 12 and the outer sheet 13. The upper protruding portion of the inner sheet 11 is folded outward (to a non-face-facing side) so as to cover the upper edges of the intermediate sheet 12 and the outer sheet 13 to form an upper folded part 11U, and the lower protruding portion is folded outward (to a non-face-facing side) so as to cover the lower edges of the intermediate sheet 12 and the outer sheet 13 to form a lower folded part 11L. As a result, either or both of the upper edge and the lower edge of the sheets constituting the mask body 10 are covered, such that even if the edges of the sheets are sharp, the face or the hand is not likely to be touched by the edges, thereby improving the wearing feeling.

In the mask body 10, a shape retention member (also called a nose fit) NF that is a flat band-like metal or resin member extending in the horizontal direction D2 may be set. For example, it is preferable to set the shape retention member NF on the surface of the outer sheet 13 before the upper folded part 11U is folded back, and set it between the upper folded part 11U and the outer sheet 13.

The pair of ear hooks 20*a* and 20*a* are joined to the mask body 10 via joining regions BD and BD at the ends of the mask body 10 in the left-right direction D2, respectively. The pair of ear hooks 20*a* and 20*a* are formed in a sheet shape, not in a string shape or a thread shape. That is, the pair of ear hooks 20*a* and 20*a* each form a band-like ring having a width in a plan view. Therefore, when the mask 1 is worn such that the ear enters an opening 29 of the ear hook 20*a*, the ear hook 20*a* comes into surface contact with the back of the ear or the back surface of the earlobe, making it possible to reduce a load on the ear. In addition, the sheet-shaped ear hooks 20*a* and 20*a* have a larger surface area than that of a string-like structure, such that the fragrance ingredient released from the fragrance carrier 35 can easily adhere to them. Therefore, the intended function can also be exhibited at the ear hooks 20*a* and 20*a*.

Further, as illustrated in FIG. 7, the pair of ear hooks 20*a* and 20*a* may be formed in the form of a single sheet in which they are separably joined to each other in the center in the horizontal direction D2, that is, in the form of one continuous ear hook sheet 20.

It is preferable that the ear hooks 20*a* and 20*a* (or the ear hook sheet 20) are formed of a member including a stretchable member and low stretchable or non-stretchable sheet-shaped surface materials placed on both surfaces of the stretchable member. More specifically, it is possible to form the stretchable ear hooks 20*a* and 20*a*, by laminating the low stretchable or non-stretchable sheets (surface materials) on both surfaces of the stretchable member while stretching the stretchable member with application of a tensile force, fixing the stretchable film and the surface materials at intermittent positions, and then removing the tensile force to free the stretchable member from the stretched state. The stretchable member may be an elastic stretchable member such as a stretchable film, a plurality of thread rubbers, and the like. In addition, the surface materials are preferably a fiber structure, more specifically a nonwoven fabric, a textile fabric, a knitted fabric, and the like, and are preferably a nonwoven fabric because a nonwoven fabric has a good feel to skin and a good breathability and contributes to improvement of the wearing feeling.

When starting to use the mask 1, the user may open the parts of the ear hooks 20*a* and 20*a* that are not joined to the mask body 10 at the joining regions BD and BD to the sides (in the horizontal direction D2) before wearing the mask 1, to bring about the state illustrated in FIG. 8. As described above, when the ear hooks 20*a* and 20*a* are joined to each other at a joining part 28, the joining is removed, to separate the ear hooks 20*a* and 20*a* from each other.

In the mask 1 illustrated in FIGS. 7 to 9, the ear hooks 20*a* and 20*a* are joined to the surface of the mask body 10 on the non-face-facing side (outer side). Therefore, in the operation of separating the ear hooks 20*a* and 20*a* from each other and opening them outward in the horizontal direction D2 as described above, the probability of the user touching the face-facing side of the mask body 10 can be reduced or eliminated, which is preferable from the hygienic viewpoint. In addition, since the ear hooks 20*a* and 20*a* facilitate both sides of the mask body 10 being pressed against the face from the non-face-facing side (outer side) during wearing of the mask 1, the gap between the mask body 10 and the face can be reduced at both sides of the mask body 10, thereby improving the mask functions (blocking of foreign matter, prevention of droplet splashing, and the like). In addition, since the end of the ear hook 20*a* does not come into direct contact with the face of the wearer during wearing, the discomfort is also reduced.

The ear hooks 20*a*, 20*a* may be provided with plucking parts 25, 25 that can be plucked by the user when separating the ear hooks 20*a*, 20*a* from each other and opening them outward in the horizontal direction D2 (FIGS. 1 and 2, and FIG. 4). The plucking parts 25, 25 allow the user to pluck the plucking parts 25, 25 with both hands without or with little contact with the mask body 10 itself. Therefore, even in a situation where the user cannot be sufficiently careful about hand hygiene, the mask 1 in a good hygienic condition can be worn by him/herself or others. The plucking parts 25 and 25 can also be used to adjust the position and tension of the ear hooks 20*a* and 20*a* when or after the ear hooks 20*a* and 20*a* are hooked on the wearer's ears.

<Sensation-Inducing Agent>

In the present embodiment, a sensation-inducing agent capable of inducing a predetermined sensation may be applied to the mask 1, preferably to the mask body 10. The sensation-inducing agent is preferably, for example, an agent that induces a sensation felt via the skin, such as a sense of coolness (or a sense of coldness), a sense of warmth, and the like, and more preferably an agent that induces a sense of coolness. It is suitable to use an endothermic substance as the sensation-inducing agent that induces a sense of coolness. The endothermic substance touches the moisture contained in the wearer's breath and causes an endothermic reaction, which lowers the temperature of the space formed between the mask and the face, thereby enabling the wearer to feel a sense of coolness. From the viewpoint of ensuring safety, it is preferable to use sugar alcohols such as xylitol, erythritol, dextrose, sorbitol, and the like, sugars such as trehalose, sucrose, lactose, maltose, and the like as the sensation-inducing agent to induce a sense of coolness. Of these, xylitol is preferable from the viewpoint of operability, and effect and efficacy.

The position on the mask 1 to which the sensation-inducing agent is applied is not particularly limited, yet it is preferable to apply the sensation-inducing agent inside the mask body 10, i.e., a non-exposed part of the mask body 10. As a result, it is possible to inhibit an excessively strong sensation induction via the skin of the wearer, and to inhibit undesirable effects that may be caused by direct contact of the sensation-inducing agent with the skin (face, fingers, and the like) in a case where the wearer has a sensitive skin. Further, it is preferable that the sensation-inducing agent 40 (FIG. 9) is applied to the outer surface (non-face facing surface) 11*ex* of the inner sheet (face-facing sheet) 11 among the sheets included in the mask body 10. Since the inner sheet 11 is the sheet that is positioned closest to the face of the wearer during wearing among the sheets (the inner sheet 11, the intermediate sheet 12, and the outer sheet 13) constituting the mask body 10, it is within easy reach of the wearer's breath, and facilitates reaction between the moisture in the wearer's breath and the sensation-inducing agent 40.

It is possible to apply the sensation-inducing agent 40 to the sheet, by applying a solution obtained by dissolving the sensation-inducing agent in a solvent, by, for example, spraying, brushing, a bar coater, a gravure coater, a flexography coater, a roll coater, inkjet printing, or the like.

The region to which the sensation-inducing agent 40 is applied is not particularly limited, and it may be applied to the entirety or a part of the surface of a sheet (nonwoven fabric, or the like) included in the mask body 10. Here, in a case of applying the sensation-inducing agent to the entirety of the mask body 10, it is unnecessary to sectionalize a sheet into an application region and a non-application region before forming the mask body from the sheet, advantageously enhancing the operability of the mask body 10 and, consequently, of the mask 1.

In a case where the sensation-inducing agent 40 is an endothermic substance, sensation induction occurs through a reaction with moisture as described above, such that the wearer feels a sense of coolness after some time has passed, rather than immediately after wearing the mask. Therefore, the function can be effectively exhibited exactly when the wearer may feel, for example, a sense of damp or a choking sense after some time has passed since the mask was worn.

Here, in a case where a sensation-inducing agent that induces a sense of coolness is used as the sensation-inducing agent 40 and a fragrance (mint oil, menthol, camphor, or the like) that also induces a sense of coolness is used as the fragrance carried on the above-mentioned fragrance carrier 35, it is possible to make the wearer feel a sense of coolness both by the fragrance ingredient transferred to the mask 1 in the package 50 and by the sensation-inducing agent 40 applied directly to the mask 1, thereby enhancing the effect of inducing a sense of coolness. Furthermore, since sensation induction by the sensation-inducing agent 40 occurs after some time has passed since the start of wearing as described above in a case where the sensation-inducing agent 40 is an endothermic substance, it is possible to make the wearer feel a sense of coolness stepwise by the fragrance and by the sensation-inducing agent 40. That is, since the fragrance is volatile, the wearer is likely to feel the fragrance immediately after wearing the mask, but the effect may not be sustained for a long time. On the other hand, since the sensation-inducing agent (endothermic substance) 40 exerts its function after some time has passed, the wearer can feel a sense of coolness as if it made up for the loss of the sense of coolness induced by the fragrance in the initial stage of wearing. By combining the fragrance and the sensation-inducing agent 40, it is possible to sustain a sensation referred to as a sense of coolness for a long time from the initial stage of wearing the mask 1.

Specific aspects of the present invention will be described below.

APPENDIX 1

An embodiment according to Appendix 1 is a mask package, including: a mask; a package configured to enclose the mask; and a bag placed in the package and enveloping a fragrance carrier carrying a fragrance.

In the embodiment according to Appendix 1, the fragrance carrier is enveloped in the bag. Thus, during storage of the mask before the start of use, the fragrance is gradually released outside the bag and transferred to the mask. Since the fragrance is not directly applied to the mask, the fragrance will not smell excessively strong in the initial stage of wearing, and the wearer can feel the fragrance of a moderate strength from the mask. In addition, since the fragrance carrier carrying the fragrance is used, the fragrance can volatilize without being pressed or tapped from outside the package. That is, it is possible to transfer the fragrance to the mask by simply placing the package under a normal storage state without applying impacts to the package. The user may apply impacts if he/she wants a strong scent to be transferred as soon as possible depending on the user's preference.

APPENDIX 2

In the embodiment according to Appendix 2, the bag includes an inner bag made of a fiber structure and an outer bag made of a polymer film and positioned on an outer side of the inner bag.

In the embodiment according to Appendix 2, since the inner bag of the bag is made of the fiber structure, volatile components of the fragrance are released from the entirety of the inner bag without the fragrance carrier coming into direct contact with the mask, and the released components attach to the mask. Therefore, the entire mask can be scented at a moderate density. In addition, since the outer bag made of a polymer film is provided on the outer side of the inner bag, it is possible to adjust the release rate of the fragrance ingredient.

APPENDIX 3

In the embodiment according to Appendix 3, a hole is formed in the outer bag.

In the embodiment according to Appendix 3, the fragrance ingredient can be released through the hole in the outer bag regardless of the material from which the outer bag is made. Therefore, as the material of the outer bag, a material having low permeability of the fragrance ingredient can also be used, and the range of material selection is widened.

APPENDIX 4

In the embodiment according to Appendix 4, information regarding the fragrance or the bag is added to an outer surface of the inner bag by a coloring agent.

In the embodiment according to Appendix 4, the information is added to the outer surface of the inner bag by a coloring agent, thereby making it possible to avoid the bag being used by the user for a wrong use. In addition, since the coloring agent is covered with the outer bag, it is possible to prevent the coloring agent from adhering to the mask or the inner wall of the package.

APPENDIX 5

In the embodiment according to Appendix 5, the fragrance carrier is of porous particles carrying the fragrance.

In the embodiment according to Appendix 5, since the carrier is a porous body, the fragrance can be carried also in the pores of the carrier. Therefore, it is possible to have a relatively large amount of the fragrance carried, and to dissipate the fragrance gradually over a long period of time. Furthermore, since the fragrance carrier is particulate, it is allowed a certain extent of fluidization in the bag. Therefore, it is possible to accelerate dissipation of the fragrance ingredient by moving the package.

APPENDIX 6

In the embodiment according to Appendix 6, the mask is coated with a sensation-inducing agent capable of inducing a predetermined sensation in a user.

In the embodiment according to Appendix 6, by applying the sensation-inducing agent directly to the mask, it is possible to make the mask wearer enjoy the effect of the sensation-inducing agent in addition to being allowed to feel the scent transferred from the fragrance in the bag to the mask, making it possible to provide a more comforting mask.

APPENDIX 7

In the embodiment according to Appendix 7, a sensation which the fragrance is capable of inducing and the sensation which the sensation-inducing agent is capable of inducing are senses of coolness.

In the embodiment according to Appendix 7, a fragrance that induces a sense of coolness is used as the fragrance and an agent that also induces a sense of coolness is used as the sensation-inducing agent. Therefore, both the fragrance and the sensation-inducing agent improve the effect of inducing in the mask wearer, a sensation referred to as a sense of coolness.

APPENDIX 8

In the embodiment according to Appendix 8, the sensation-inducing agent is an endothermic substance.

In the embodiment according to Appendix 8, the sensation-inducing agent that is an endothermic substance can lower the temperature in the space between the mask and the face when the mask is worn, and the wearer can feel a sense of coolness. In addition, since the reaction of the endothermic substance usually takes some time to occur rather than occurring immediately after wearing, a sense of comfort (sense of coolness) can be provided to the wearer when some time has passed since the start of wearing and the wearer may begin to feel hotness, a choking sense, and the like. By combining such a sensation-inducing agent with the fragrance described above, it is possible to make the scent transferred to the mask in the package be felt in the initial stage of wearing, and then a sense of coldness or a sense of coolness induced by the sensation-inducing agent be felt after some time has passed, thereby sustaining a sense of comfort from the initial stage of wearing until any timing during wearing. Furthermore, in a case where a fragrance that induces a sense of coolness is selected as the fragrance as in the embodiment of Appendix 7, the predetermined sensation referred to as the sense of coolness can be maintained for a long time from the initial stage of wearing by the fragrance and the sensation-inducing agent.

Although the present invention has been described above based on the embodiments, the present invention is not limited by these embodiments. In addition, various changes, modifications, substitutions, additions, deletions, combinations, and the like are applicable to the above embodiments within the scope described in the claims, and they are also included within the technical scope of the present invention.

The present application claims priority under Japanese Patent Application No. 2022-066773 filed Apr. 14, 2022, the entire contents of which are hereby incorporated herein.

REFERENCE SIGNS LIST

1 mask
10 mask body
11 inner sheet (face-facing sheet)
11U upper folded part of an inner sheet
11L lower folded part of an inner sheet
12 intermediate sheet
13 outer sheet
15 pleats
20 ear hook sheet

20*a* ear hook
25 plucking part
28 separable joining part
29 opening
30 bag
31 outer bag
31*h* hole in an outer bag
32 inner bag
34 information
35 fragrance carrier (fragrance-carrying particles)
50 package
51 first sheet of a package
51*a* folded part of a first sheet
52 second sheet of a package
100 mask package
BD joining region
D1 vertical direction (upper-lower direction)
D2 horizontal direction (left-right direction)
NF shape retention member

The invention claimed is:

1. A mask package, comprising:
a mask;
a package configured to enclose the mask; and
a bag placed in the package and enveloping a fragrance carrier carrying a fragrance,
wherein the bag includes an inner bag made of a fiber structure and an outer bag made of a polymer film and positioned on an outer side of the inner bag,
wherein the fiber structure of the inner bag is made of an air-permeable material, and a hole is formed in the outer bag.

2. The mask package according to claim 1,
wherein information regarding the fragrance or the bag is added to an outer surface of the inner bag by a coloring agent.

3. The mask package according to claim 1,
wherein the fragrance carrier is of porous particles carrying the fragrance.

4. The mask package according to claim 1,
wherein the mask is coated with a sensation-inducing agent capable of inducing a predetermined sensation in a user.

5. The mask package according to claim 4,
wherein a sensation which the fragrance is capable of inducing and the sensation which the sensation-inducing agent is capable of inducing are senses of coolness.

6. The mask package according to claim 5,
wherein the sensation-inducing agent is an endothermic substance.

* * * * *